United States Patent
Duffill et al.

(10) Patent No.: US 7,421,350 B2
(45) Date of Patent: Sep. 2, 2008

(54) METER ELECTRONICS AND METHOD FOR DETECTING A RESIDUAL MATERIAL IN A FLOW METER ASSEMBLY

(75) Inventors: Graeme Ralph Duffill, Boulder, CO (US); Andrew Timothy Patten, Boulder, CO (US); Mark James Bell, Arvada, CO (US)

(73) Assignee: Micro Motinn, Inc., Boulder, CO (US)

( * ) Notice: Subject to any disclaimer, the term of this patent is extended or adjusted under 35 U.S.C. 154(b) by 0 days.

(21) Appl. No.: 11/570,314

(22) PCT Filed: Jun. 22, 2004

(86) PCT No.: PCT/US2004/019938

§ 371 (c)(1),
(2), (4) Date: Dec. 8, 2006

(87) PCT Pub. No.: WO2006/009348

PCT Pub. Date: Jan. 26, 2006

(65) Prior Publication Data

US 2007/0186682 A1    Aug. 16, 2007

(51) Int. Cl.
*G01F 1/76* (2006.01)
*G06F 17/00* (2006.01)

(52) U.S. Cl. ............... 702/50; 702/45; 702/48; 702/54; 73/861.356

(58) Field of Classification Search ........... 702/50, 702/45, 48, 54, 56, 100, 103
See application file for complete search history.

(56) References Cited

U.S. PATENT DOCUMENTS

| | | | |
|---|---|---|---|
| 4,884,441 A | 12/1989 | Lew | |
| 4,992,952 A | 2/1991 | Sasaki | |
| 5,275,061 A | 1/1994 | Young et al. | |
| 5,316,444 A | 5/1994 | Wicnienski | |
| 5,918,285 A * | 6/1999 | Van der Pol | 73/861.357 |
| 6,272,438 B1 * | 8/2001 | Cunningham et al. | 702/56 |
| 6,327,914 B1 | 12/2001 | Dutton | |
| 6,556,931 B1 * | 4/2003 | Hays et al. | 702/54 |
| 6,834,241 B2 * | 12/2004 | Hays et al. | 702/45 |

FOREIGN PATENT DOCUMENTS

| | | |
|---|---|---|
| EP | 0816807 A2 | 1/1998 |
| JP | 2003-194610 | 7/2003 |

\* cited by examiner

*Primary Examiner*—Hal D Wachsman
(74) *Attorney, Agent, or Firm*—The Ollila Law Group LLC

(57) ABSTRACT

A meter electronics and method for detecting a residual material in a flow meter assembly are provided according to the invention. The meter electronics includes a processing system adapted to direct the flow meter to vibrate the flow meter assembly and receive a vibrational response from the flow meter assembly. The meter electronics further includes a storage system configured to store flow meter parameters and data. The meter electronics is further characterized by the processing system being configured to compare the vibrational response to a predetermined residual material threshold to detect the residual material.

22 Claims, 8 Drawing Sheets

METER ELECTRONICS AND METHOD FOR DETECTING A RESIDUAL MATERIAL IN A FLOW METER ASSEMBLY

BACKGROUND OF THE INVENTION

1. Field of the Invention

The invention is related to the field of flow meters, and in particular, is related to detecting a residual material in a flow meter assembly of a flow meter.

2. Statement of the Problem

Flowmeters are used to measure the mass flow rate, density, and other characteristics of flowing materials. The flowing materials can comprise liquids, gases, combined liquids and gases, solids suspended in liquids, and liquids including gases and suspended solids. For example, flowmeters are used in industrial processes for measuring quantities of ingredients and resultant products by measuring a flow rate (i.e., by measuring a mass flow through the flowmeter).

One type of flow meter is a Coriolis flow meter. It is known to use Coriolis mass flow meters to measure mass flow and other information of materials flowing through a pipeline as disclosed in U.S. Pat. No. 4,491,025 issued to J. E. Smith, et al. of Jan. 1, 1985 and Re. 31,450 to J. E. Smith of Feb. 11, 1982. These flow meters have one or more flow tubes of different configurations. Each conduit configuration may be viewed as having a set of natural vibration modes including, for example, simple bending, torsional, radial and coupled modes. In a typical Coriolis mass flow measurement application, a conduit configuration is excited in one or more vibration modes as a material flows through the conduit, and motion of the conduit is measured at points spaced along the conduit. The vibrational modes of the material filled systems are defined in part by the combined mass of the flow tubes and the material within the flow tubes. When there is no material flowing through the flow meter, all points along a flow tube oscillate with an identical phase. As a material begins to flow through the flow tube, Coriolis accelerations cause each point along the flow tube to have a different phase with respect to other points along the flow tube. The phase on the inlet side of the flow tube lags the driver, while the phase on the outlet side leads the driver. Sensors are placed at different points on the flow tube to produce sinusoidal signals representative of the motion of the flow tube at the different points. A phase difference of the signals received from the sensors is calculated in units of time. The phase difference between the sensor signals is proportional to the mass flow rate of the material flowing through the flow tube or flow tubes.

A problem exists in the prior art in determining whether any residual material remains in a flow meter. When a flow meter is allowed to self-drain, some moisture may remain within a flow tube. This is especially true in a closed environment. The flow meter may comprise a flow meter that employs a straight flow tube apparatus, wherein an amount of residual material can remain in the flow tube apparatus and not drain. Alternatively, a flow meter may employ an arc or loop-shaped flow tube apparatus. The shape of such a flow tube apparatus can trap a significant amount of residual material and can present additional challenges in ensuring that a process fluid has totally drained from the flow meter. In addition, the installation orientation of the flow meter can contribute to retention of residual material, wherein the residual material is unable to adequately or completely drain out of the flow meter.

In some applications, particularly within the pharmaceutical, biotech, and food and beverage industries, it is critical to ensure that a flow meter has totally self-drained and is free of flow media.

SUMMARY OF THE SOLUTION

The invention helps solve the above problems by providing a meter electronics and method for detecting a residual material in a flow meter assembly.

A meter electronics adapted for detecting a residual material in a flow meter assembly is provided according to an embodiment of the invention. The meter electronics comprises a processing system adapted to direct the flow meter to vibrate the flow meter assembly and receive a vibrational response from the flow meter assembly. The meter electronics further comprises a storage system configured to store flow meter parameters and data. The flow meter electronics is further characterized by the processing system being configured to compare the vibrational response to a predetermined residual material threshold to detect the residual material.

A method of detecting a residual material in a flow meter assembly is provided according to an embodiment of the invention. The method comprises vibrating the flow meter assembly and measuring a vibrational response of the flow meter assembly. The method is further characterized by comparing the vibrational response to a predetermined residual material threshold to detect the residual material.

In one aspect of the invention, the predetermined residual material threshold is user-settable.

In another aspect of the invention, the detecting further comprises substantially determining a residual material mass value.

In another aspect of the invention, the processing system is further configured to generate an alarm condition if the vibrational response exceeds the predetermined residual material threshold.

In another aspect of the invention, the processing system is further configured to determine an empty condition in the flow meter assembly if the vibrational response does not exceed the predetermined residual material threshold.

In another aspect of the invention, the processing system is further configured to additionally compare a drive amplitude and a drive gain and detect the residual material if the vibrational response exceeds the predetermined residual material threshold and if the drive gain exceeds the drive amplitude by a gain threshold.

In another aspect of the invention, the flow meter comprises a Coriolis flow meter.

In another aspect of the invention, the processing system is further configured to initially store a fundamental vibration frequency for the flow meter and determine the predetermined residual material threshold from the fundamental vibration frequency, with the predetermined residual material threshold comprising a predetermined frequency offset from the fundamental vibration frequency.

In another aspect of the invention, the processing system is further configured to determine a compensated frequency from the vibrational response, calculate a frequency difference between the compensated frequency and a fundamental vibrational frequency of the flow meter; and multiply the frequency difference by a mass-frequency relationship factor to obtain a residual material mass value for the flow meter assembly, wherein the comparing comprises comparing the residual material mass value to the predetermined residual material threshold.

In another aspect of the invention, the predetermined residual material threshold comprises a calibration density value of the flow meter assembly and with the processing system being further configured to compensate the vibrational response to produce a compensated density value, wherein the comparing comprises comparing the compensated density value to the calibration density value and wherein the detecting comprises detecting the residual material if the compensated density value substantially matches the calibration density value.

In another aspect of the invention, the processing system is further configured to compensate the vibrational response to produce a compensated density value and multiply the compensated density value by a flow tube volume, by a coupling factor that defines a flow media viscosity coupling characteristic, and by an orientation factor in order to produce a residual material mass value. The predetermined residual threshold comprises a predetermined residual mass threshold. The comparing comprises comparing the residual material mass value to the predetermined residual material threshold.

In another aspect of the invention, the compensating further comprises compensating the vibrational response for ambient temperature and ambient pressure.

DESCRIPTION OF THE DRAWINGS

The same reference number represents the same element on all drawings.

DETAILED DESCRIPTION OF THE INVENTION

FIGS. 1-8 and the following description depict specific examples of the invention to teach those skilled in the art how to make and use the best mode of the invention. For the purpose of teaching inventive principles, some conventional aspects of the invention have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
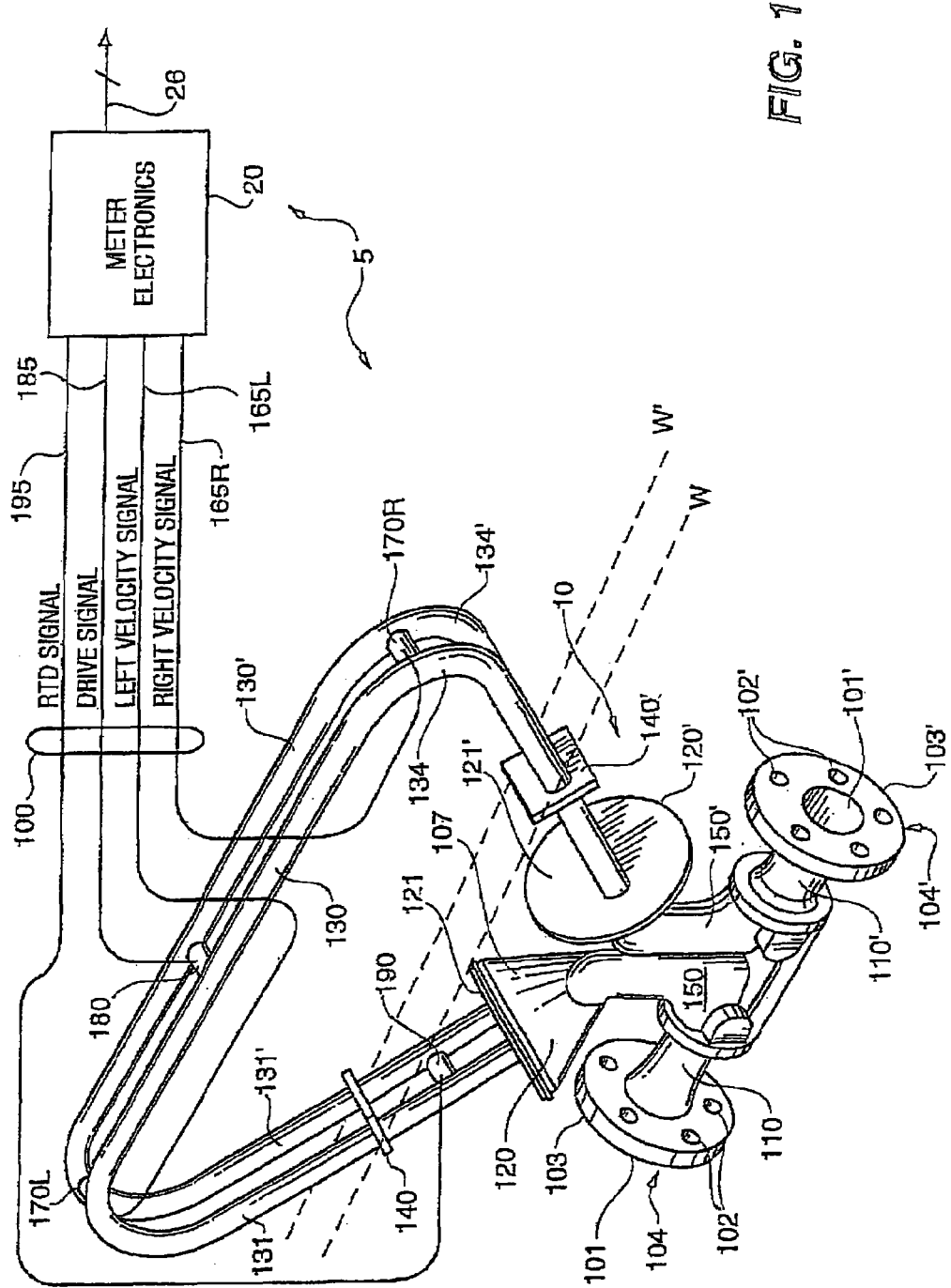
FIG. 1 shows a Coriolis flow meter comprising a flow meter assembly and meter electronics according to an embodiment of the invention.

Flow Meter—FIG. 1

FIG. 1 shows a Coriolis flow meter 5 comprising a flow meter assembly 10 and meter electronics 20 according to an embodiment of the invention. The Coriolis flow meter 5 is provided as an example, and it should be understood that the invention applies to other flow meter configurations and other flow meter types. Flow meter assembly 10 responds to mass flow rate and density of a process material. Meter electronics 20 is connected to flow meter assembly 10 via leads 100 to provide density, mass flow rate, and temperature information over path 26, as well as other information. A Coriolis flow meter structure is described although it is apparent to those skilled in the art that the present invention could be practiced as a vibrating tube densitometer without the additional measurement capability provided by a Coriolis mass flow meter. In addition, the invention may apply to other flow meter types.

Flow meter assembly 10 can include a pair of manifolds 150 and 150', flanges 103 and 103' having flange necks 110 and 110', a pair of parallel flow tubes 130 and 130', drive mechanism 180, temperature sensor 190, and a pair of pick-off sensors 170L and 170R. Flow tubes 130 and 130' have two essentially straight inlet legs 131 and 131' and outlet legs 134 and 134' which converge towards each other at flow tube mounting blocks 120 and 120'. Flow tubes 130 and 130' bend at two symmetrical locations along their length and are essentially parallel throughout their length. Brace bars 140 and 140' serve to define the axis W and W' about which each flow tube oscillates.

The side legs 131, 131' and 134, 134' of flow tubes 130 and 130' are fixedly attached to flow tube mounting blocks 120 and 120' and these blocks, in turn, are fixedly attached to manifolds 150 and 150'. This provides a continuous closed material path through Coriolis flow meter assembly 10.

When flanges 103 and 103', having holes 102 and 102' are connected, via inlet end 104 and outlet end 104' into a process line (not shown) which carries the process material that is being measured, material enters end 104 of the meter through an orifice 101 in flange 103 is conducted through manifold 150 to flow tube mounting block 120 having a surface 121. Within manifold 150 the material is divided and routed through flow tubes 130 and 130'. Upon exiting flow tubes 130 and 130', the process material is recombined in a single stream within manifold 150' and is thereafter routed to exit end 104' connected by flange 103' having bolt holes 102' to the process line (not shown).

Flow tubes 130 and 130' are selected and appropriately mounted to the flow tube mounting blocks 120 and 120' so as to have substantially the same mass distribution, moments of inertia, and Young's modulus about bending axes W—W and W'—W', respectively. These bending axes go through brace bars 140 and 140'.

Because the Young's modulus of the flow tubes change with temperature, and this change affects the calculation of flow and density, the temperature sensor 190, such as a resistive temperature detector (RTD), can be mounted to flow tube 130' in order to measure the temperature of the flow tube. The temperature of the flow tube is governed by the temperature of the material passing through the flow tube. The measured temperature is used in a well known method by meter electronics 20 to compensate for the change in elastic modulus of flow tubes 130 and 130' due to any changes in flow tube temperature. The temperature sensor 190 is connected to meter electronics 20 by lead 195.

Both flow tubes 130 and 130' are driven by driver 180 in opposite directions about their respective bending axes W and W' and at what is termed the first out-of-phase bending mode of the flow meter. This drive mechanism 180 may comprise any one of many well known arrangements, such as a magnet mounted to flow tube 130' and an opposing coil mounted to flow tube 130 and through which an alternating current is passed for vibrating both flow tubes. A suitable drive signal is applied by meter electronics 20, via lead 185, to drive mechanism 180.

Meter electronics 20 receives the temperature signal on lead 195, and the left and right pick-off signals appear on leads 165L and 165R, respectively. Meter electronics 20 produces the drive signal appearing on lead 185 to drive element 180 and vibrate tubes 130 and 130'. Meter electronics 20 processes the left and right pick-off signals and the temperature signal to compute the mass flow rate (and optionally the density) of the material passing through flow meter assembly 10. This information, along with other information, is applied by meter electronics 20 over path 26.

Figure 2:
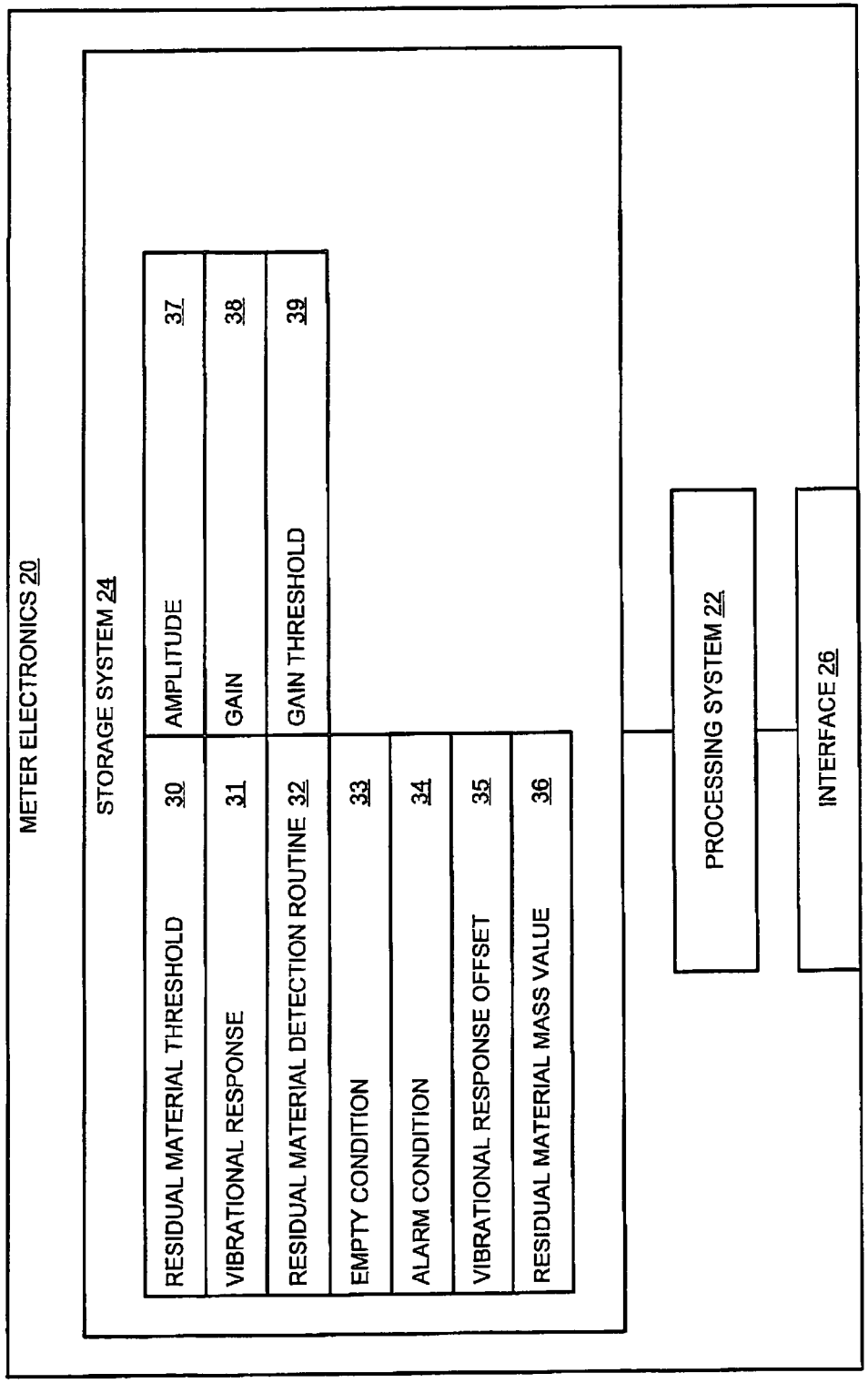
FIG. 2 is a diagram of meter electronics according to an embodiment of the invention.

Meter Electronics—FIG. 2

FIG. 2 is a diagram of meter electronics 20 according to an embodiment of the invention. The meter electronics 20 includes a processing system 22 and a storage system 24 connected to the processing system 22. An interface 26 can be included in the meter electronics 20, and is also connected to the processing system 22.

The meter electronics 20 receives flow meter signals from the flow meter assembly 10 (see FIG. 1) and can determine whether the flow meter assembly 10 is empty or non-empty. In one embodiment, the invention can obtain a vibrational frequency response 31 and compare the vibrational response 31 to a frequency threshold or range in order to determine an empty or non-empty condition of the flow meter assembly 10 (see FIG. 4 and the accompanying discussion). In another embodiment, the vibrational response 31 can be used to determine a residual material mass, and the residual material mass can be compared to a mass threshold or range in order to determine an empty or non-empty state (see FIG. 4 and the accompanying discussion). The mass can additionally be used to determine the amount of residual material in the flow meter assembly 10. In addition, a residual material density can be compared to a density threshold or range in order to determine an empty or non-empty state (see FIG. 6 and the accompanying discussion).

The detection of residual material can have several uses. One use is in determining when the flow meter assembly 10 is empty, where the flow meter 5 is used to measure a fluid supply in some manner of fluid handling system. For example, where the flow meter 5 measures the output of a fluid reservoir, the meter electronics 20 and method can be used to determine when a fluid flow from the reservoir has been shut off. Another use is to detect an end of a fluid flow and therefore detect when the reservoir is empty. Yet another use is a momentary operation of the flow meter 5 in order to determine whether the flow meter 5 is empty.

The interface 26 conducts communications with other devices. The interface 26 comprises any device capable of communicating with one or more flow meters. In addition, the interface 26 can enable communications over telephone systems and/or digital data networks. Consequently, the meter electronics 20 can communicate with remote flow meters, remote memory media, and/or remote users.

In one embodiment, the interface 26 receives signals from the flow meter assembly 10, including signals representative of the vibrational response 31 of the flow meter 5. The meter electronics 20 therefore can be co-located with or remote from the flow meter assembly 10. In another embodiment, the interface 26 enables a human operator to interact with the meter electronics 20. As a result, the interface 26 can accept operator inputs and can transmit outputs to the operator.

In one embodiment, the interface 26 can receive operator inputs, including a residual material threshold 30 that is used to determine whether the flow meter assembly 10 is empty or non-empty. Consequently, the residual material threshold 30 in this embodiment is user-settable. Alternatively, the residual material threshold 30 can be a fixed value or a factory-set value.

In one embodiment, the interface 26 can additionally generate outputs to an operator. An output can comprise a determination of whether the flow meter assembly 10 is empty or non-empty. An output can comprise an approximate mass of any residual material in the flow meter assembly 10. An output can comprise an alarm condition that alerts the operator to a residual material in the flow meter assembly 10. The alarm condition can be generated when the residual material in the flow meter assembly 10 is greater than the residual material threshold 30. The output can comprise any manner of visual, audio, or textual information.

The processing system 22 conducts operations of the meter electronics 20. The processing system 22 can comprise a general purpose computer, a microprocessing system, a logic circuit, or some other general purpose or customized processing device. The processing system 22 can be distributed among multiple processing devices. The processing system 22 can include any manner of integral or independent electronic storage medium, such as the storage system 24.

The storage system 24 can comprise any manner of digital storage medium. The storage system 24 can store flow meter parameters and data, software routines, constant values, and variable values. In one embodiment, the storage system 24 includes a residual material threshold 30, a vibrational response 31, a residual material detection routine 32, an empty condition 33, an alarm condition 34, a vibrational response offset 35, a residual material mass value 36, a drive amplitude 37, a drive gain 38, and a gain threshold 39.

The processing system 22 executes the residual material detection routine 32 and thereby determines whether the flow meter assembly 10 is empty or non-empty. In one embodiment, the residual material detection routine 32 is part of the meter electronics 20, as shown. The residual material detection routine 32, when executed by the processing system 22, configures the processing system 22 to compare the vibrational response 31 to the residual material threshold 30. The residual material detection routine 32 therefore detects residual material in the flow meter assembly 10 if the vibrational response 31 exceeds the residual material threshold 30.

In another embodiment, the residual material detection routine 32 comprises data and instructions that are incorporated into a software platform running on an external device (not shown). This external device is capable of communicating with the meter electronics 20 over the communication path 26. For example, the external device can comprise an external computer running a software such as PROLINK or PROLINK II. The PROLINK software is designed for communicating with flow meters and for logging and manipulating flow meter output, and is available from Micro Motion Inc. of Boulder, Colo. The PROLINK software is just one useful software platform, and it should be understood that the residual material detection according to the invention can be implemented in any suitable software language or platform and on any suitable external device.

The residual material threshold 30 in one embodiment comprises a threshold that is used by the residual material detection routine 32 to determine if residual material is present in the flow meter assembly 10. The residual material threshold 30 is also used to determine whether a residual material in the flow meter assembly 10 is significant enough in amount to be considered as residual material and therefore is non-empty.

In one embodiment, the residual material threshold 30 comprises an offset from an empty state vibrational response (i.e., the fundamental vibrational frequency of the flow meter assembly 10). The empty state vibrational response can comprise a vibrational response recorded for an empty condition of the flow meter assembly 10 when filled with air, at a specific ambient air temperature and at a specific ambient air pressure (i.e., at standard calibration conditions). Therefore, when the flow meter assembly 10 is in a clean dry air state at a specific temperature, the fundamental/resonant frequency of the device can be determined. The empty state vibrational response can subsequently serve as a standard against which subsequent vibrational responses can be compared in order to detect empty and non-empty conditions of the flow meter assembly 10. Therefore, in an application situation, a significant deviation from the temperature corrected air states resonant frequency indicates the presence of process material. Consequently, if the vibrational response 31 exceeds the residual material threshold 30, then residual material is detected. Alternatively, the residual material threshold 30 comprises a residual material range, wherein if the vibrational response falls within the range, then the flow meter assembly 10 is non-empty but is empty enough to comprise merely residual material (i.e., the flow meter assembly 10 is not full). If the vibrational response exceeds this range, then material is flowing through the flow meter assembly 10 in a normal manner of use.

The vibrational response 31 is received from the flow meter assembly 10. The vibrational response 31 comprises a measured or detected response to the vibration of the flow tube or tubes by the driver 180. The vibrational response 31 will vary with the amount of material that is present in the flow meter assembly 10. The vibrational response 31 can be stored as an analog frequency response measured by the one or more pickoff sensors 170.

The vibrational response offset 35 can comprise an offset from an empty state vibrational response. The vibrational response offset 35 therefore comprises an offset from an empty condition, wherein if the vibrational response 31 does not fall between the vibrational response offset 35 and the empty state vibrational response, then the flow meter assembly 10 is non-empty. The vibrational response offset 35 can comprise a frequency offset, a density offset, or a mass value offset, for example, as discussed herein and as discussed below in conjunction with FIGS. 4-8.

In addition to the use of the vibrational response for detecting residual material, the vibrational response 31 can also be used to estimate a residual material mass value 36. The residual material mass value 36 comprises a substantially current mass value as determined for the flow meter assembly 10. In addition, the residual material mass value 36 can be used to determine whether the flow meter assembly 10 is empty or non-empty. Moreover, the residual material mass value 36 can be output to an operator, etc., in order to indicate the approximate mass of the residual material. Furthermore, the residual material mass value 36 in one embodiment can store a historical record of mass flow rates during empty and non-empty conditions and corresponding time periods.

The empty condition 33 can comprise a state variable that can represent empty and non-empty states, such as by true and false states, for example. Therefore, if a current vibrational response of the flow meter assembly 10 is judged to be an empty state, then the empty condition 33 can be set to a true, one, or other empty state. Conversely, if a current vibrational response of the flow meter assembly 10 is judged to be a non-empty state, then the empty condition 33 can be set to a false, zero, or other non-empty state. The empty condition 33 therefore reflects a current empty or non-empty condition of the flow meter assembly 10. In addition, the empty condition 33 in one embodiment can store a historical record of empty and non-empty conditions and corresponding time periods.

The alarm condition 34 can comprise a state variable that can be generated when the residual material exceeds the residual material threshold 30. The alarm condition 34 therefore can be used to alert a user or operator of residual material in the flow meter assembly 10. In addition, the alarm condition 34 can be used as a process control variable, wherein subsequent process actions can be disabled or modified if the alarm condition 34 is set. The alarm condition 34 in one embodiment can store a historical record of alarm and non-alarm conditions and corresponding time periods. Moreover, the alarm condition 34 in one embodiment encompasses a user-settable alarm threshold, wherein the user can determine the amount of residual material at which an alarm condition will be set by the meter electronics 20.

In addition to the vibrational response 31, the meter electronics 20 in this and any embodiment of the invention can further monitor a drive signal amplitude applied to the drive mechanism 180. Furthermore, the meter electronics 20 can also monitor a drive gain received from the pick-off 170, where the drive gain comprises a relationship between the drive signal amplitude supplied to the drive mechanism 180 and the resulting vibrational response 31. The amplitude and gain indicate the amount of vibrational energy absorbed by residual material, and can be used to further refine the residual material detection. Consequently, the drive signal gain and drive signal amplitude can be used to further refine the determination of the residual material mass value 36. Therefore, the processing system 22 in one embodiment is further configured to additionally compare a drive amplitude 37 and a drive gain 38 and detect the residual material if the vibrational response 31 exceeds the predetermined residual material threshold 30 and if the drive gain 38 exceeds the drive amplitude 37 by a gain threshold 39.

Figure 3:
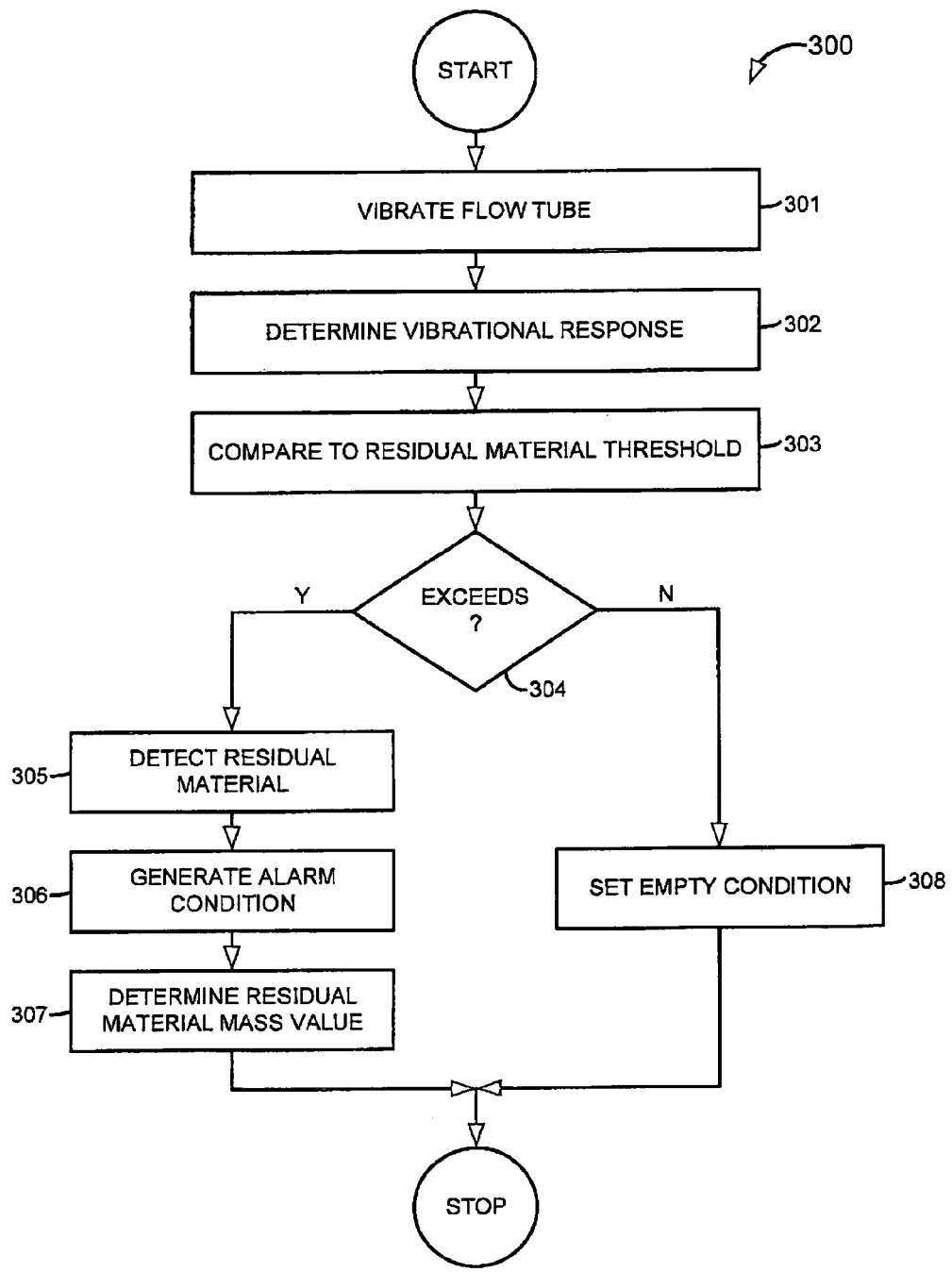
FIG. 3 is a flowchart of a method of detecting a residual material in a flow meter assembly according to an embodiment of the invention.

Detection Method Flowchart—FIG. 3

FIG. 3 is a flowchart 300 of a method of detecting a residual material in a flow meter assembly according to an embodiment of the invention. In step 301, the flow meter assembly 10 is vibrated with a driver vibration. The vibration can comprise a fundamental frequency of the flow meter assembly 10. The driver vibration therefore can comprise a typical vibration used to detect mass flow in the flow meter assembly 10.

In step 302, the vibrational response of the flow meter assembly 10 is determined. The vibrational response is typically received in the form of an electrical signal wherein the signal amplitude varies in relationship to a mass of material present or flowing in the flow meter assembly 10. The electrical signal can be processed in order to obtain mass and density values for the material in the tube. In addition, unlike the prior art, the electrical signal can be processed in order to determine the presence of and the approximate amount of residual material in the flow meter assembly 10.

In step 303, the vibrational response of the flow meter assembly 10 is compared to a residual material threshold in order to detect residual material. In one embodiment, the residual material threshold can comprise a flow tube empty state vibrational response. The flow tube empty state vibrational response can be measured for the flow tube at the factory, for example. The flow tube empty state vibrational response is typically generated for a standard temperature and pressure. The flow tube empty state vibrational response can therefore comprise a benchmark for all subsequent residual material detection operations. Alternatively, the residual material threshold can comprise an offset from the flow tube empty state vibrational response, as previously discussed, and can comprise a frequency, density, or mass value or range.

In step 304, if the vibrational response exceeds the residual material threshold, the vibrational response is determined to denote a non-empty condition and the method branches to step 305. Alternatively, if the vibrational response does not exceed the residual material threshold, the flow meter assembly 10 is determined to be empty and the method branches to step 308.

In step 305, because the vibrational response exceeds the residual material threshold, then residual material is detected in the flow meter assembly 10. The detection can include setting an empty condition state to non-empty. In addition, the detection can include recording a historical record of non-empty condition occurrences and corresponding time periods. As a result, the non-empty condition can be used to determine whether the flow meter assembly 10 needs to be inspected, cleaned, maintained, repaired, etc.

In step 306, an alarm condition can be optionally generated. The alarm condition can include visual, audio, or textual alarms presented to a user or operator, as previously discussed. The alarm condition can occur at a beginning of a residual material detection, or alternatively can continue as long as residual material is present in the flow meter assembly 10.

In step 307, the method can optionally determine a residual material mass value. The residual material mass value can be recorded. The residual material mass value can be used to determine whether the flow meter 5 is empty or non-empty.

In step 308, where the flow meter assembly 10 is determined to be empty, an empty condition state can be set to empty. In addition, the detection can include recording a historical record of empty condition occurrences and corresponding time periods.

Figure 4:
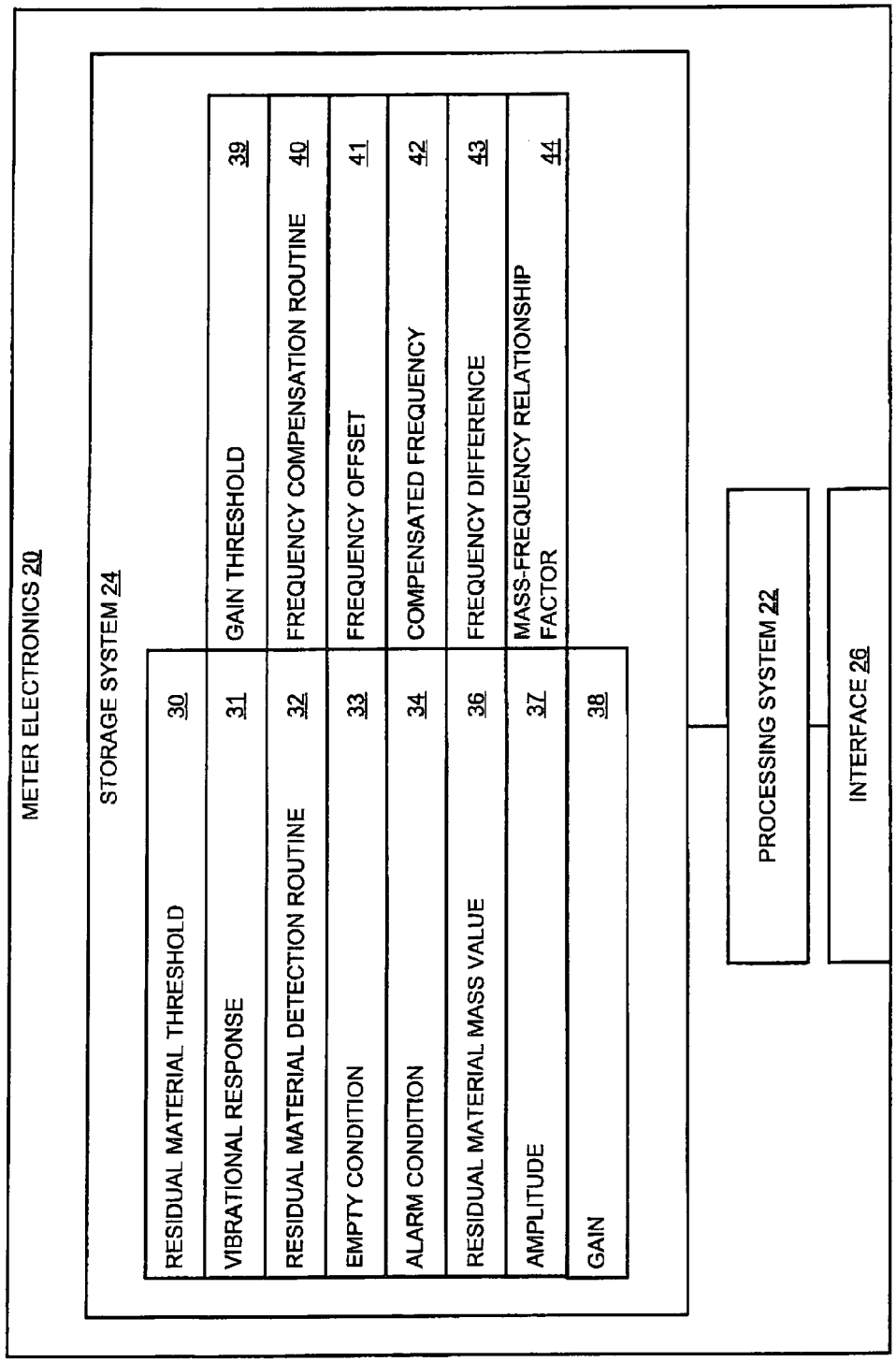
FIG. 4 is a diagram of meter electronics according to an embodiment of the invention.

Meter Electronics—FIG. 4

FIG. 4 is a diagram of meter electronics 20 according to an embodiment of the invention. The meter electronics 20 can include a processing system 422, a storage system 24, and an interface 426, as previously discussed.

The storage system 24 can include a residual material threshold 30, a frequency offset 41, a compensated frequency 42, a frequency difference 43, a mass-frequency relationship factor 44, a residual material mass value 36, and a frequency compensation routine 40. The storage system 24 can further include, as previously discussed, a vibrational response 31, a residual material detection routine 32, an empty condition 33, an alarm condition 34, a drive amplitude 37, a drive gain 38, and a gain threshold 39.

In operation, the meter electronics 20 receives the vibrational response 31 and determines if the vibrational response 31 indicates an empty or non-empty flow meter assembly 10. The meter electronics 20 in this embodiment can provide such a determination by comparing the vibrational response 31 to a frequency threshold or range or by determining a mass value from the vibrational response 31 and comparing the mass value to a mass threshold or range. For example, in the latter embodiment, the meter electronics 20 generates a residual material mass value 36 related to any residual material in the flow meter assembly 10 and determines if the residual material mass value 36 rises to the level of residual material. It should be understood that if the residual material mass value 36 is very small, the residual material mass value 36 can simply be treated as an empty flow meter assembly 10.

A density measurement of a Coriolis flow meter is based on the equation:

$$2\pi f = 2\pi/\tau = \sqrt{(k/m)} \quad (1)$$

where:
- k=the stiffness of the flow meter assembly,
- m=the mass of the flow meter assembly,
- f=the frequency of oscillation (of the vibrational response), and
- τ=the period of oscillation.

More specifically, the resonant frequency of the flow meter assembly 10 is proportional to the stiffness of the flow tube or flow tubes, and is inversely proportional to the coupled mass (i.e., the mass of the flow meter assembly 10 plus the mass of any fluid media within and therefore coupled to the flow meter assembly 10).

The residual material threshold 30 stores a fundamental vibrational frequency of the flow meter assembly 10 for a standard air (empty) condition. This corresponds to an empty condition for the flow meter assembly 10.

The frequency offset 41 is a frequency offset threshold from the fundamental vibrational (i.e., empty) frequency. The frequency offset 41 is used to determine whether the vibrational response 31 is close enough to the fundamental vibrational frequency for the flow meter assembly 10 to be considered as empty.

The compensated frequency 42 comprises the vibrational response of the flow meter assembly 10 after the vibrational response 31 has been compensated for the ambient temperature and the ambient air pressure. The compensation can additionally compensate the vibrational response 31 for other factors, such as flow tube geometry and characteristics, etc. The compensation in this embodiment is performed by the frequency compensation routine 40 (see discussion below).

The frequency difference 43 comprises a difference between the compensated frequency 42 and the residual material threshold 30. The frequency difference 43 is calculated as a prelude to determining the residual material mass value 36.

The mass-frequency relationship factor 44 is a mathematical model that maps the frequency difference 43 to a mass value. The mass-frequency relationship factor 44 can comprise a mathematical formula in one embodiment. In another embodiment, the mass-frequency relationship factor 44 can comprise a data structure, such as a data table, that maps an input frequency difference to an output mass value (i.e., it produces the residual material mass value 36).

The mass-frequency relationship factor 44 can be selected according to the material to be measured by the flow meter 5. Accordingly, the mass-frequency relationship factor 44 can vary between different fluid media. The mass-frequency relationship factor 44 can be programmed into the storage system 24, such as at the factory or by an operator if the flow material is to be changed.

The residual material mass value 36 comprises a mass value determined from the current vibrational response 31. The residual material mass value 36 reflects the approximate mass of residual material in the flow meter assembly 10.

The frequency compensation routine 40 operates on the vibrational response 31 and performs compensation on the vibrational response 31 in order to increase accuracy of the flow meter 5. The compensation can comprise any manner of compensation. In one embodiment, the compensation comprises temperature compensation and pressure compensation, wherein the vibrational response 31 is compensated for ambient temperature and ambient pressure in order to approximate an accuracy of standard conditions of temperature and pressure. In addition, the frequency compensation routine 40 can employ other, pre-measured and pre-stored calibration factors in the compensation process.

Figure 5:
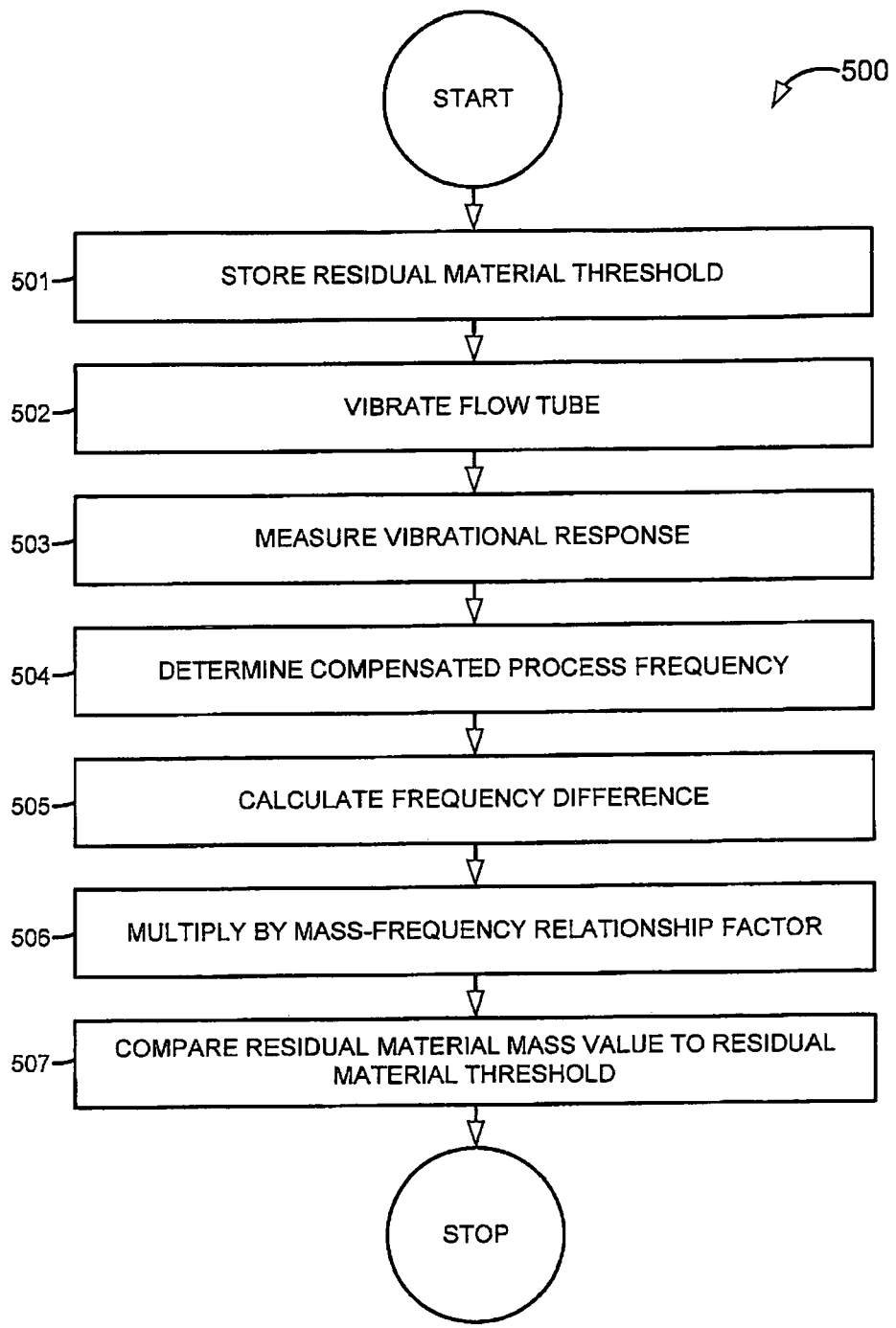
FIG. 5 is a flowchart of a method of detecting a residual material in a flow meter assembly according to an embodiment of the invention.

Detection Method Flowchart—FIG. 5

FIG. 5 is a flowchart 500 of a method of detecting a residual material in a flow meter assembly according to an embodiment of the invention. The method 500 in one embodiment comprises a method of operating the meter electronics 20 of FIG. 4. In step 501, the residual material threshold is stored. In this method embodiment, the residual material threshold can comprise a fundamental vibrational frequency. The residual material threshold can be stored at any time before the following step.

In step 502, the flow tube or flow tubes are vibrated in order to detect the presence of residual material, as previously discussed.

In step 503, the flow meter 5 measures the vibrational response, as previously discussed.

In step 504, a compensated frequency is determined from the vibrational response. The compensated frequency can comprise a vibrational frequency compensated for temperature, pressure, flow tube geometry and characteristics, etc. Additionally, other types of compensation can also be performed on the vibrational response.

In step 505, a frequency difference is calculated between the compensated frequency of the flow meter assembly 10 and the fundamental vibrational frequency. Ideally, if the flow meter assembly 10 is completely empty, the compensated frequency will match the fundamental vibrational frequency and the difference will be zero. However, there is a probability that the frequency difference may be non-zero, even when the flow meter assembly 10 is substantially empty. Therefore, in one embodiment the frequency difference must exceed a threshold before a non-empty state can be practically determined.

In step 506, the compensated frequency is multiplied by a mass-frequency relationship factor in order to determine a residual material mass value.

In step 507, the residual material mass value is compared to a residual material threshold. In this embodiment, the residual material threshold comprises a mass threshold, below which the residual material mass value is considered to be empty. If the residual material mass value exceeds the residual material threshold, then the flow meter assembly 10 is determined to be non-empty.

Figure 6:
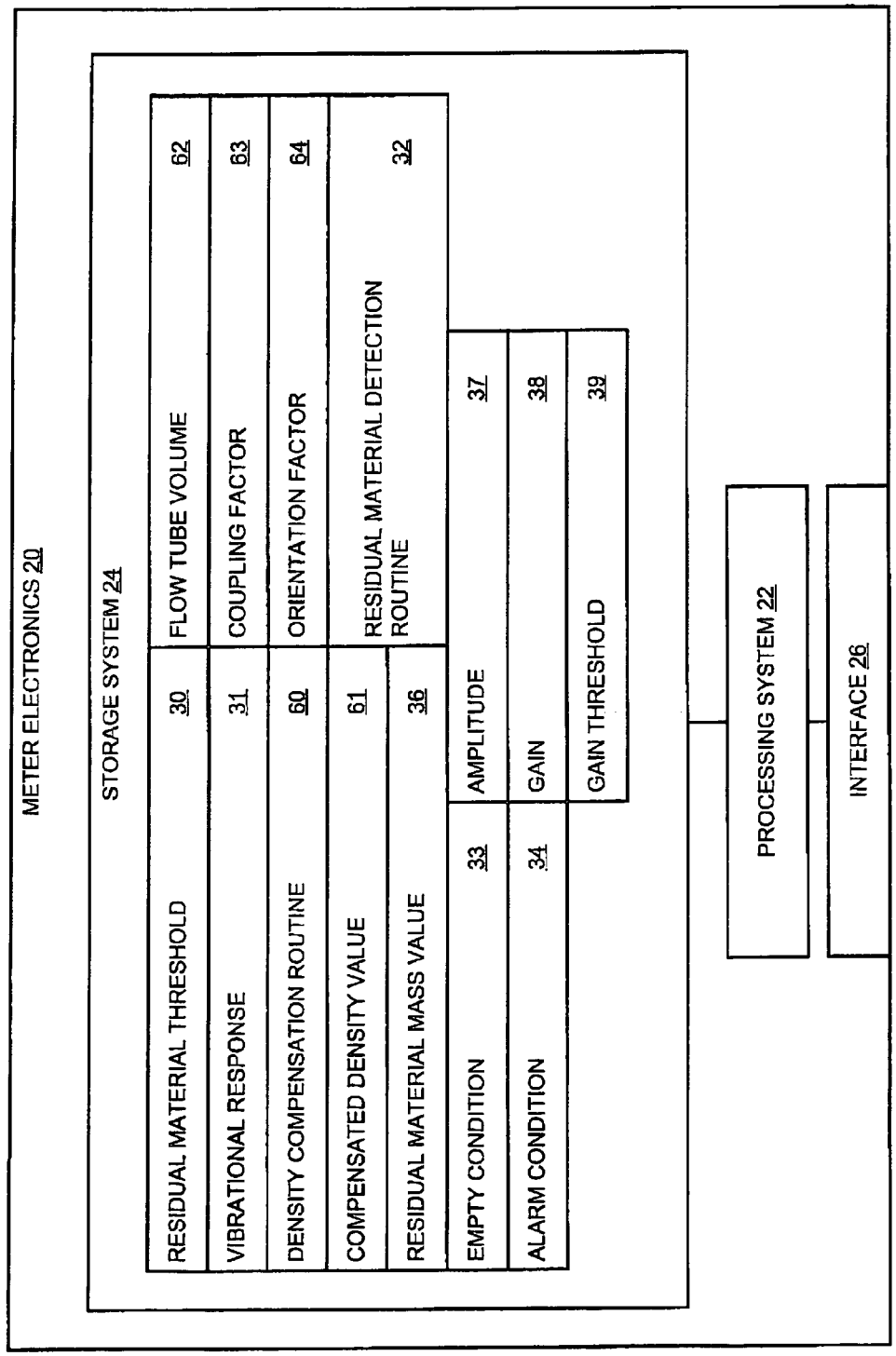
FIG. 6 is a diagram of meter electronics according to an embodiment of the invention.

Meter Electronics—FIG. 6

FIG. 6 is a diagram of meter electronics 20 according to an embodiment of the invention. The meter electronics 20 can include a processing system 622, a storage system 24, and an interface 626, as previously discussed.

The storage system 24 can include a residual material threshold 30, a density compensation routine 60, a compensated density value 61, a residual material mass value 36, a flow tube volume 62, a coupling factor 63, and an orientation factor 64. The storage system 24 can further include, as previously discussed, a vibrational response 31, a residual material detection routine 32, an empty condition 33, an alarm condition 34, a drive amplitude 37, a drive gain 38, and a gain threshold 39.

Figure 7:
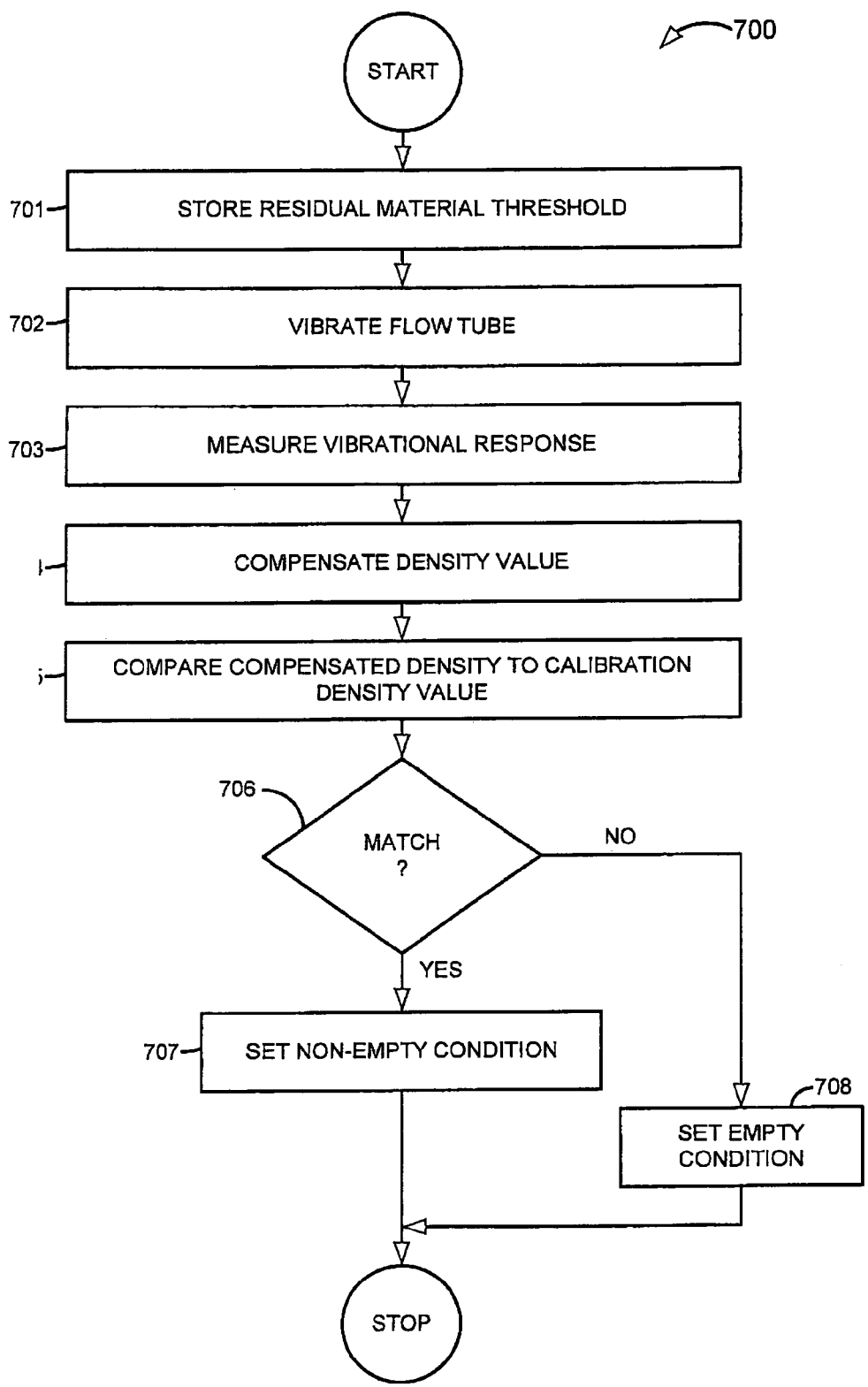
FIG. 7 is a flowchart of a method of detecting a residual material in a flow meter assembly according to an embodiment of the invention.

In operation, the meter electronics 20 receives the vibrational response 31, generates the compensated density value 61 related to a residual material in the flow meter assembly 10, and compares the compensated density value 61 to a density threshold or range (see FIG. 7).

In one embodiment, the residual material threshold 30 comprises a calibration density value or range. The calibration density value comprises a density value or density range that reflects the composition of the material flowing through the flow meter assembly 10. The calibration density value is provided for a given flow material and for a given set of conditions, such as for a standard temperature and pressure, etc. The calibration density value is typically measured under standard conditions and pre-stored, such as at the factory or during a field calibration operation. Variation from the calibration density value can be used to determine a non-empty state, and can additionally be used to detect the presence of an unanticipated or undesired flow medium in the flow meter assembly 10. If the vibrational response 31, when processed to yield the compensated density value 61, substantially matches the residual material threshold 30, then the flow meter assembly 10 can be determined to be non-empty.

The density compensation routine 60 performs a density compensation operation on a measured density in order to increase the accuracy of the flow meter 5. The density compensation routine 60 generates the compensated density value 61 from the vibrational response 31. Since the vibrational response 31 comprises a rate of density per frequency measure (i.e., $\delta\rho/\delta f$), and since density ($\rho$) comprises mass divided by volume, then the rate of change of frequency with mass (i.e., $\delta m/\delta f$) can be determined by substitution. Therefore, the vibrational response 31 comprises an electrical signal having a frequency representative of a material mass in the flow meter assembly 10.

The compensated density value 61 comprises a compensated density obtained from the vibrational response 31, as described above. The compensation can comprise any manner of compensation and is performed in order to increase accuracy of the flow meter 5. In one embodiment, the compensation comprises temperature compensation and pressure compensation, wherein the vibrational response 31 is compensated for ambient temperature and ambient pressure. In addition, the density compensation routine 60 can employ other pre-measured and pre-stored calibration factors in the compensation process.

Figure 8:
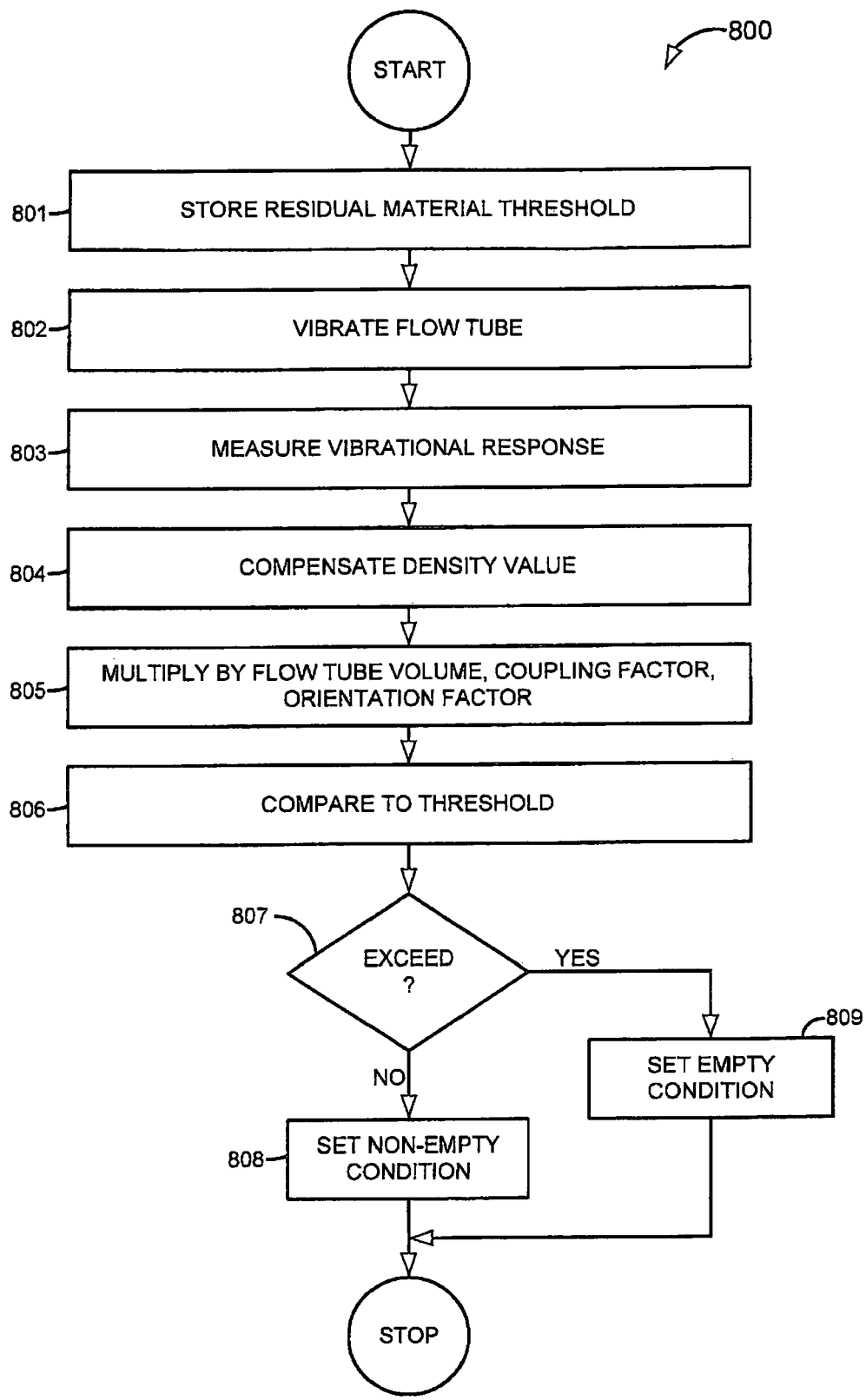
FIG. 8 is a flowchart of a method of detecting a residual material in a flow meter assembly according to an embodiment of the invention.

In addition to using the density for determining whether the flow meter assembly 10 is empty or non-empty, the density can be used to determine the residual material mass value 36 (see FIG. 8). The optional mass determination can be used to determine the amount of residual material present, and further employs the flow tube volume 62, the coupling factor 63, and the orientation factor 64. The flow tube volume 62, the coupling factor 63, and the orientation factor 64 can comprise pre-determined and/or pre-stored factors.

The flow tube volume 62 comprises a volume of a flow tube or tubes in the flow meter assembly 10. The flow tube volume 62 can vary between flow meter types and sizes, and can be unique to the particular flow meter 5.

The coupling factor 63 includes a flow material viscosity factor that correlates to the tendency of the material to cling to the inner surfaces of the flow meter assembly 10, i.e., a more viscous material will more likely cling to and not drain out of the flow meter assembly 10. The coupling factor 63 will therefore vary according to the flow material.

The orientation factor 64 comprises a factor that reflects an installation orientation of the flow meter assembly 10. The orientation factor 64 therefore changes with installation orientation of the flow meter assembly 10, as the orientation will affect the ability of the flow meter assembly 10 to drain.

Detection Method Flowchart—FIG. 7

FIG. 7 is a flowchart 700 of a method of detecting a residual material in a flow meter assembly according to an embodiment of the invention. The method 700 comprises a method embodiment for operating the meter electronics 20 of FIG. 6. In step 701, the residual material threshold is stored. In this method embodiment, the residual material threshold can comprise a calibration density value. The residual material threshold can be stored at any time before the following step.

In step 702, the flow meter assembly 10 is vibrated, as previously discussed.

In step 703, the flow meter 5 measures the vibrational response, as previously discussed.

In step 704, a compensated density value is determined, as previously discussed.

In step 705, the compensated density value is compared to the calibration density value (i.e., the residual material threshold), as previously discussed. The compensated density value can comprise a predetermined offset of the calibration density value or can comprise a density range or tolerance.

In step 706, if the compensated density value substantially matches the calibration density value, the method proceeds to step 707. Otherwise, the method branches to step 708.

In step 707, where the compensated density value substantially matches the calibration density value, it can be determined that a flow material is present in the flow meter assembly 10. Therefore, a non-empty condition can be set, as previously discussed. In addition, an alarm condition can be set, as previously discussed.

In step 708, where the compensated density value does not substantially match the calibration density value, it can be determined that a flow material is not present in the flow meter assembly 10. Therefore, an empty condition can be set, as previously discussed.

Detection Method Flowchart—FIG. 8

FIG. 8 is a flowchart 800 of a method of detecting a residual material in a flow meter assembly according to an embodiment of the invention. The method 800 comprises another method embodiment for operating the meter electronics 20 of FIG. 6. In step 801, the residual material threshold is stored. In this method embodiment, the residual material threshold can comprise a residual material mass threshold. The residual material threshold can be stored at any time before the following step.

In step 802, the flow meter assembly 10 is vibrated, as previously discussed.

In step 803, the flow meter 5 measures the vibrational response, as previously discussed.

In step 804, a compensated density value is determined, as previously discussed.

In step 805, the compensated density value is multiplied by a flow tube volume, a coupling factor, and an orientation factor, as previously discussed. The product of the multiplication is a residual material mass value.

In step 806, the residual material mass value is compared to the residual material mass threshold. The residual material mass threshold can comprise a mass range or tolerance.

In step 807, if the residual material mass value exceeds the residual material mass threshold, then the method proceeds to step 808. Otherwise, the method branches to step 810.

In step 808, where the residual material mass value exceeds the residual material mass threshold, it can be determined that a flow material is present in the flow meter assembly 10. Therefore, a non-empty condition can be set, as previously discussed. In addition, an alarm condition can be set, as previously discussed.

In step 809, where the residual material mass value does not exceed the residual material mass threshold, it can be determined that a flow material is not present in the flow meter assembly 10. Therefore, an empty condition can be set, as previously discussed.

The meter electronics and method according to the invention can be employed according to any of the embodiments in order to provide several advantages, if desired. The meter electronics and method can provide an ability to detect residual material in a flow meter. The flow meter can comprise a Coriolis flow meter, for example. The meter electronics and method can provide an ability to measure a residual material mass of a residual material in a flow meter. The residual material can be detected and/or measured at any time after a normal material flow has been terminated. For example, the flow meter can be momentarily or periodically activated in order to detect and/or measure residual material. Alternatively, the flow meter can be substantially continuously operated and can therefore detect when a normal flow has ended. Consequently, the flow meter can additionally detect when a residual material is still present or has satisfactorily drained.

The meter electronics and method according to the invention can provide an ability to set a threshold for detecting residual material in a flow meter. The threshold can be pre-configured or can be user-settable.

The meter electronics and method according to the invention can provide an alarm that is activated when residual material exceeds a threshold. The alarm can be pre-configured or alternatively can be configured or set by an operator.

What is claimed is:

1. A meter electronics adapted for detecting a residual material in a flow meter assembly of a flow meter, with the meter electronics comprising:
   a processing system adapted to direct the flow meter to vibrate the flow meter assembly and receive a vibrational response from the flow meter assembly; and
   a storage system configured to store flow meter parameters and data;
   wherein the processing system being configured to compare the vibrational response to a predetermined residual material threshold to detect the residual material, with the predetermined residual material threshold comprising a predetermined frequency response and one or both of a predetermined drive amplitude and a predetermined drive gain.

2. The meter electronics of claim 1, with the predetermined residual material threshold being user-settable.

3. The meter electronics of claim 1, with the processing system being further configured to estimate a residual material mass value.

4. The meter electronics of claim 1, with the processing system being further configured to generate an alarm condition if the vibrational response exceeds the predetermined residual material threshold.

5. The meter electronics of claim 1, with the processing system being further configured to determine an empty condition in the flow meter assembly if the vibrational response does not exceed the predetermined residual material threshold.

6. The meter electronics of claim 1, wherein the flow meter comprises a Coriolis flow meter.

7. The meter electronics of claim 1, with the processing system being further configured to initially store a fundamental vibration frequency for the flow meter assembly and determine the predetermined residual material threshold from the fundamental vibration frequency, with the predetermined residual material threshold comprising a predetermined frequency offset from the fundamental vibration frequency.

8. The meter electronics of claim 1, with the processing system being further configured to:
   determine a compensated frequency from the vibrational response;
   calculate a frequency difference between the compensated frequency and a fundamental vibrational frequency of the flow meter assembly; and
   multiply the frequency difference by a mass-frequency relationship factor to obtain a residual material mass value for the flow meter assembly;
   wherein the comparing comprises comparing the residual material mass value to the predetermined residual material threshold.

9. The meter electronics of claim 1, with the predetermined residual material threshold comprising a calibration density value of the flow meter assembly and with the processing system being further configured to:
   compensate the vibrational response to produce a compensated density value;
   wherein the comparing comprises comparing the compensated density value to the calibration density value; and
   wherein the detecting comprises detecting the residual material if the compensated density value substantially matches the calibration density value.

10. The meter electronics of claim 1, with the processing system being further configured to:
    compensate the vibrational response to produce a compensated density value; and
    multiply the compensated density value by a flow tube volume, by a coupling factor that defines a flow media viscosity coupling characteristic, and by an orientation factor in order to produce a residual material mass value;
    wherein the predetermined residual threshold comprises a predetermined residual mass threshold; and
    wherein the comparing comprises comparing the residual material mass value to the predetermined residual material threshold.

11. The meter electronics of claim 10, with the compensating further comprising compensating the vibrational response for ambient temperature and ambient pressure.

12. A method of detecting a residual material in a flow meter assembly of a flow meter, comprising:
    vibrating the flow meter assembly and measuring a vibrational response of the flow meter assembly; and
    comparing the vibrational response to a predetermined residual material threshold to detect the residual material, with the predetermined residual material threshold comprising a predetermined frequency response and one or both of a predetermined drive amplitude and a predetermined drive gain.

13. The method of claim 12, with the predetermined residual material threshold being user-settable.

14. The method of claim 12, with the detecting further comprising substantially determining a residual material mass value.

15. The method of claim 12, with the method further comprising generating an alarm condition if the vibrational response exceeds the predetermined residual material threshold.

16. The method of claim 12, with the method further comprising determining an empty condition in the flow meter assembly if the vibrational response does not exceed the predetermined residual material threshold.

17. The method of claim 12, wherein the flow meter comprises a Coriolis flow meter.

18. The method of claim 12, with the method further comprising initially storing a fundamental vibration frequency for the flow meter assembly, with the comparing comprising determining the predetermined residual material threshold from the fundamental vibration frequency and with the predetermined residual material threshold comprising a predetermined frequency offset from the fundamental vibration frequency.

19. The method of claim 12, with the comparing further comprising:
    determining a compensated frequency from the vibrational response;
    calculating a frequency difference between the compensated frequency and a fundamental vibrational frequency of the flow meter assembly; and
    multiplying the frequency difference by a mass-frequency relationship factor to obtain a residual material mass value for the flow meter assembly;
    wherein the comparing comprises comparing the residual material mass value to the predetermined residual material threshold.

20. The method of claim 12, with the predetermined residual material threshold comprising a calibration density value of the flow meter assembly and with the method further comprising:
    compensating the vibrational response to produce a compensated density value;
    wherein the comparing comprises comparing the compensated density value to the calibration density value; and
    wherein the detecting comprises detecting the residual material if the compensated density value substantially matches the calibration density value.

21. The method of claim 12, with the comparing further comprising:
    compensating the vibrational response to produce a compensated density value; and
    multiplying the compensated density value by a flow tube volume, by a coupling factor that defines a flow media viscosity coupling characteristic, and by an orientation factor that is related to an installation orientation of the flow meter assembly to produce a residual material mass value;
    wherein the predetermined residual material threshold comprises a predetermined residual mass threshold; and
    wherein the comparing comprises comparing the residual material mass value to the predetermined residual material threshold.

22. The method of claim 12, with the compensating further comprising compensating the vibrational response for ambient temperature and ambient pressure.

* * * * *

UNITED STATES PATENT AND TRADEMARK OFFICE
CERTIFICATE OF CORRECTION

| | |
|---|---|
| PATENT NO. | : 7,421,350 B2 |
| APPLICATION NO. | : 11/570314 |
| DATED | : September 2, 2008 |
| INVENTOR(S) | : Graeme Ralph Duffill, Andrew Timothy Patten and Mark James Bell |

It is certified that error appears in the above-identified patent and that said Letters Patent is hereby corrected as shown below:

Item (73) Assignee:
replace "Micro Motinn, Inc., Boulder, CO (US)
with --Micro Motion, Inc., Boulder, CO (US)--

Signed and Sealed this

Twenty-third Day of December, 2008

JON W. DUDAS
*Director of the United States Patent and Trademark Office*